United States Patent [19]

Prohaska

[11] Patent Number: 5,027,499

[45] Date of Patent: Jul. 2, 1991

[54] METHOD FOR FABRICATING A CHANNEL DEVICE AND TUBE CONNECTION

[75] Inventor: Otto J. Prohaska, Cleveland Heights, Ohio

[73] Assignee: Otto Sensors Corporation, Cleveland, Ohio

[21] Appl. No.: 341,641

[22] Filed: Apr. 21, 1989

Related U.S. Application Data

[62] Division of Ser. No. 936,887, Dec. 2, 1986, abandoned.

[30] Foreign Application Priority Data

Dec. 9, 1985 [AT] Austria ............................. A3562/85

[51] Int. Cl.$^5$ .............................................. G01R 3/00
[52] U.S. Cl. ........................................ 29/595; 29/424; 156/644
[58] Field of Search ................ 29/593, 423, 424, 852, 29/853, 846, 595; 156/644, 656, 659.1, 661.1, 901, 902; 204/406, 411, 424, 425; 427/96, 97, 264, 265; 73/864.83, 864.84, 866, 863.84

[56] References Cited

U.S. PATENT DOCUMENTS

| | | | |
|---|---|---|---|
| 4,293,522 | 10/1981 | Winkler | 204/424 X |
| 4,391,152 | 7/1983 | Ellett | 73/863.84 |
| 4,534,825 | 8/1985 | Koning et al. | 156/644 |
| 4,545,851 | 10/1985 | Takada | 156/644 X |
| 4,734,184 | 3/1988 | Burleigh et al. | 204/411 X |
| 4,741,817 | 5/1988 | Croset et al. | 204/425 |

*Primary Examiner*—Timothy V. Eley
*Assistant Examiner*—Peter Dungba Vo
*Attorney, Agent, or Firm*—Calfee, Halter & Griswold

[57] ABSTRACT

The invention is concerned with a method for manufacturing a channel device, especially for recordings of thermal conductivity, viscosity, density, dielectric constants, refractive indices, etc. of materials such as fluids and gases (called samples), where the material under investigation is guided through a measuring channel with at least one sensor and at least one inlet and one outlet orifice for the sample. The invention also concerns the fabrication procedure of the channel device, especially the recording unit for determining the thermal conductivit, viscosity, density, dielectric constant, etc. of samples where the material under investigation is passed through or brought into a measuring channel which is equipped with sensors and actuators.

15 Claims, 3 Drawing Sheets

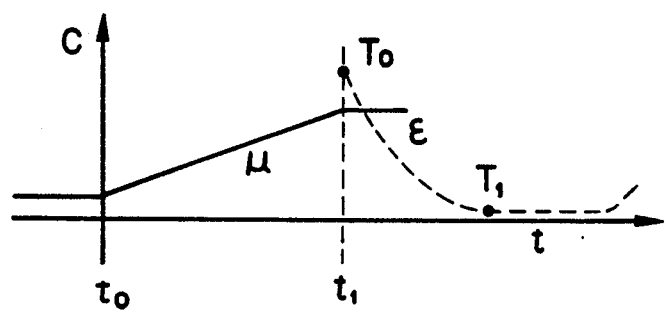
FIG. 2A
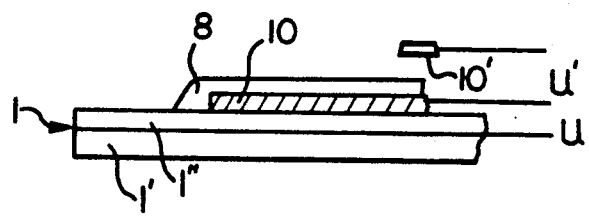
FIG. 2B
FIG. 3
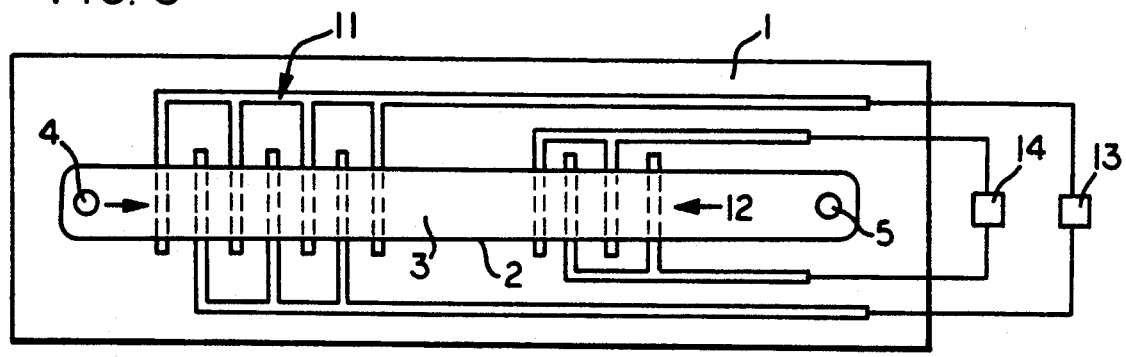
FIG. 3A
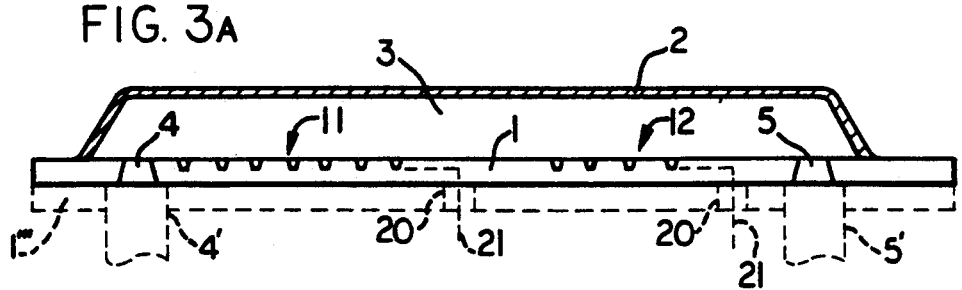

METHOD FOR FABRICATING A CHANNEL DEVICE AND TUBE CONNECTION

This is a divisional of co-pending application Ser. No. 06/936,887 filed on Dec. 2, 1986. Now abandoned.

BACKGROUND OF THE INVENTION

The invention is concerned with a channel device, especially for recordings of thermal conductivity, viscosity, density, dielectric constants, refractive indices, etc. of materials such as fluids and gases (called samples), where the material under investigation is guided through a measuring channel with at least one sensor and at least one inlet and one outlet orifice for the sample. The invention also concerns the fabrication procedure of the channel device, especially the recording unit for determining the thermal conductivity, viscosity, density, dielectric constant, etc. of samples where the material under investigation is passed through or brought into a measuring channel which is equipped with sensors and actuators.

The aim of the invention is to create a measuring arrangement capable of on-line recordings which is extremely sensative even for a very small sample volume and can be miniaturized for mass production, using photolithographic, thin-film and solid-state techniques. The invention is characterized by a channel, formed by a substrate (or carrier) and a layer, forming a wall, which is arranged a certain distance from the substrate. The layer is deposited by evaporation, spin-on, sputter, drop-on, reactive deposition, CVD, PECVD, etc., techniques and consists ie. of synthetic material, glass, ceramic, Si3N4, SiO2, SiO, combinations of these materials, etc. The invention is also characterized by the fact that the sensors and actuators are formed by layers on and/or in the substrate and /or in the wall forming layer, ie. by evaporation, spin-on, sputter, drop-on, reactive deposition, CVD (chemical vapor deposition), PECVD (plasma enhanced chemical vapor deposition), etc. techniques.

The process invention is characterized as follows: a dissolvable substance is deposited on the substrate, forming the inside of the channel, consisting of ie. photoresist, synthetic material etc. The dissolvable substance is covered afterwards by the wall forming layer, which also covers at least parts of the substrate where the substrate is free of dissolvable substance. The layer adheres well on the substrate and forms, together with the substrate, the measuring channel. The dissolvable substance can be dissolved and removed through the inlet and outlet orifices using solvents and solutions which are not dissolving or attacking the wall forming layer or the substrate.

BRIEF DESCRIPTION OF THE DRAWINGS

FIGS. 2 and 2b depict a cross-sectional view of a channel device for measuring viscosity and dielectric constants;

FIG. 2a is a graph depicting the slope of capacitance change and velocity of a sample in the calculation of viscosity;

FIG. 3 is a schematic of a device consisting of a transmitter and receiver for measuring sample density;

FIG. 3a is a cross-secional view showing the location of the transmitter and receiver relative to the substrate;

DETAILED DESCRIPTION

Furthermore, it is the aim of the invention to establish connections to thin tubes in order to conduct fluids or gases in or out of the miniaturized measuring arrangements such as described, ie., in this invention. The invented tube connection is characterized by the fact that onto at least one tube, which can be connected to the substrate (ie. glued on), at least one layer is deposited ie. by evaporation, drop-on procedure, sputtering, spin-on, reactive deposition, CVD, PECVD. etc., in such a way that the endings of the tubes are kept open and the layer is tightly connected with the tube and the substrate and establishes and defines a free space together with the substrate in such a way that this free space becomes a continuation of the inside of the tube.

The fabrication procedure for such a connection is characterized, according to the invention, in that a dissolvable substance, ie. photoresist, synthetic resin, etc., is deposited onto a substrate as well as into a tube which can be mounted (ie. glued) onto the substrate in such a way that this dissolvable substance forms a continuation of the tube. A layer is then deposited onto the dissolvable substance so that it covers this substance as well as at least a part of the tube and at least a part of the substrate and forms a tight and sealing connection with the tube as well as with the substrate. The deposition of the layer may be performed by evaporation, drop-on, sputtering, spin-on reactive deposition, CVD, PECVD, etc. The dissolvable substance can be dissolved and removed through the open end(s) of the tube and/or through the open end of the continuation which was formed by the dissolvable substance, using a solvent or procedure which will not affect the substrate or the layer or the tube.

Preferred designs of the tube connections and procedures for the fabrication of these connections can be found in the subclaims, the description and the drawings.

The evaluation and analysis of the measurements if performed by electronic devices which are connected to sensors and actuators which are arranged in and/or on the layer and/or in and/or on the substrate. The temperature raise of the heating layers, the creation of surface accoustic waves and all other actuations which are necessary for proper recordings, can be generated by appropriate electronic devices.

It is easy to see that recording arrangements, which are differing from the ones described above, and can be produced, using the invented fabrication techniques, ie. miniaturized chromatographs, pH-meters, pressure sensors, etc.

Figure 1:
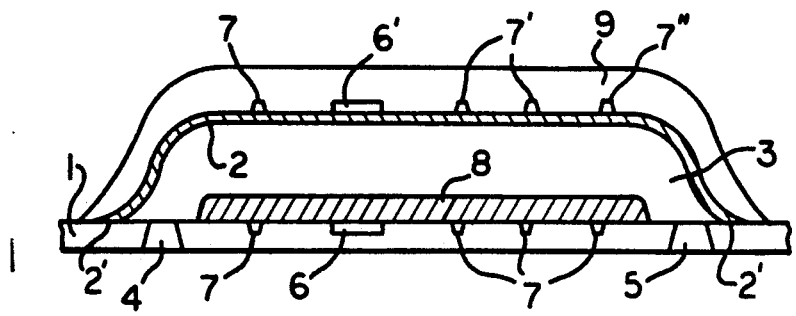
FIGS. 1a, 1b and 1c depict a cross-sectional view of the channel device of the present invention.

The selection of the dissolvable substances and their solvents can, to a large extent, be left to specialists. The schematic drawings will explain the invention: FIG. 1 shows a channel device which is especially designed for recording thermal conductivity and viscosity of a fluid or a gas. A layer(2) is deposited on a substrate(1) in such a way that a measuring channel is formed which has at least one inlet orifice(4) and one outlet orifice(5). The layer(2) is deposited onto the substrate(1) in such a way that a dissolvable substance is first deposited which has the shape of the measuring channel(3) on top of which the layer(2) is deposited, covering the dissolvable substance and at least parts of the substrate(1), so called boundary parts(2'), on which the layer(2) adheres tightly. Then, the dissolvable substance will be dissolved through the inlet and/or outlet orifices(4,5). Thus, the measuring channel(3) is formed by the substrate(1) and the layer(2). Actuators and/or sensors can be arranged on and/or in the substrate(1) and/or on and/or in the layer(2) in order to equip the measuring channel(3) with the desirable recording, sensing, and/or actuating units. The various sensor and/or acutator layers on and/or in the substrate(1) as well cover layers(8) on the substrate(1) are to be deposited before the deposition of the dissolvable substance. It is, however, possible to subsequently passivate the inside of the measuring channel(3) by inserting cover layers(8") (FIG. 1c) or to increase the measuring channel(3) by etching or to modify the characteristics of the actuators and/or sensors by appropriate surface treatments. Heating layers (6,6') are shown as an example in FIG. 1 in an indentation in the substrate(1) and on the layer(2), which can be formed by evaporation, implantation, doping, etc. The electrical connections to these actuators are not shown. Temperature sensors (7,7') are arrranged in the substrate(1) and on the layer (2). The temperature sensors(7,7') can consist of semiconductor layers, doped layers, metal layers, etc. FIG. 1c shows the layers 6' and 7' as being contained in layer(2); they can also be covered by a cover layer(8"). That is possible in particular if the layer(2) or the substrate(1) consists of silicon which can be formed into a sensor or actuator by doping or reactive deposition. in this case the layer(2) or the substrate(1) is part and/or basis for the sensor of acuator units.

Figure 1A:
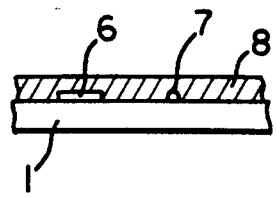

The layers (6 and 7) can be, as shown in FIG 1, deposited in indentations in the substrate(1) or on the substrate(1) (FIG. 1a). The layers (6 and 7) can also be covered by a cover layer(8) in order to prevent modifications of the layers (6 and 7). Another layer (9) can be put on top of layer (2) and the layers (6' and 7') which can also be thicker to mechanically stabilize the channel device.

The deposition of the layers (2,8,9,8' etc) can be performed by drop on, or spread on, sputtering, evaporation, spin on, etc procedures. The thickness of the layer(2) is advantageously between 1 um and 50 um, the height of the measuring channel(3) up to 50 um, the width of the measuring channel(3) can be between 1 um and 500 um and the length might be up to several 10 mm. These values can be changed, however, depending on the various applications. In most cases it might be advantageous to have the height of measuring channel(3) much smaller than the width in order to provide an optimum contact between the sample and the sensors and actuators. The thickness of the sensor and actuator layers is usually in the range of 0.2 um and 40 um.

Figure 1B:
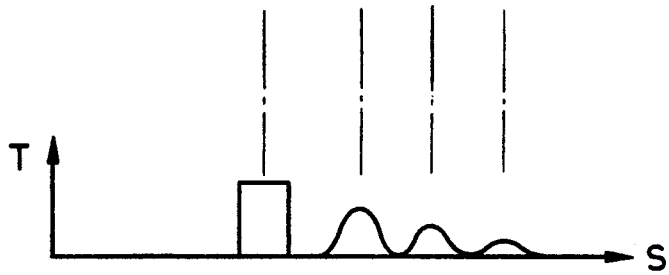
Figure 1C:
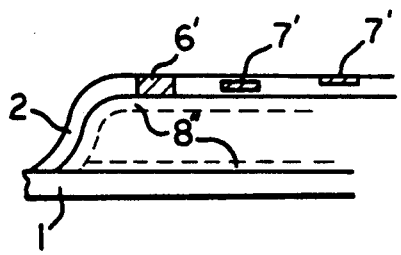

The viscosity measurement (FIG. 1b) is performed by applying a heat pulse through the heating layer (6,6') onto the sample gas or liquid, which flows through the measuring channel, and measuring the resulting temperature change of the sample with the temperature sensors 7 and/or 7'. The time between the heat pulse application and the temperature change, measured with the sensors 7 or 7' determines the velocity of the sample in the solution which, in turn, is inverse proportion to the viscosity. The pressure difference between the inlet(4) and outlet(5) of the measuring channel(3) has to be known or controlled and can be measured with pressure sensors(7"). Pressure sensors can be avoided in case of using a reference measuring channel(3) and the same pressure difference in both channels. Thermal conductivity can be measured by applying a certain amount of heat with a certain amplitude course and detecting the occurance of the temperature maximums, the amplitude course and the decrease of the maximum at the temperature sensors (7) (FIG. 1c).

Figure 2:
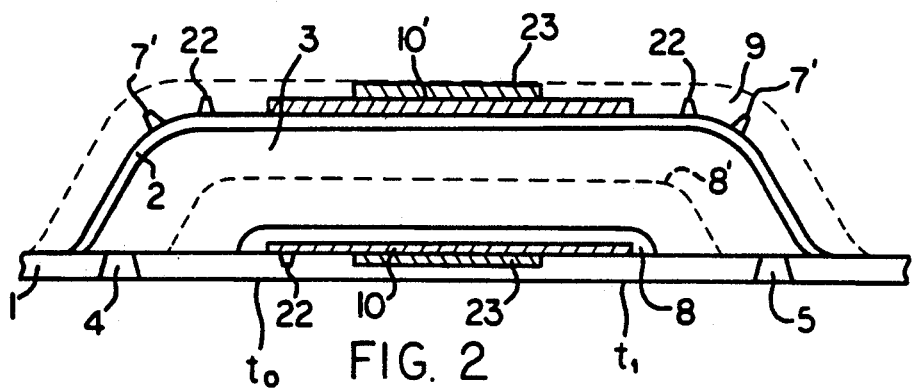

All the explanations for FIG. 1 are in principle valid also for the following figures and the described characteristics can be combined with the following ones:

FIG. 2 shows a channel device for recording viscosity and/or dielectric constants. This channel device is in principle designed similar to the one described in FIG. 1: conducting layers(10,10') are deposited on the substrate(1) and the layer(2), forming a capacitor. As soon as the sample moves into and through the measuring channel(3), which was previously filled with air or was evacuated, the capacitance of the layers(10,10') will be changed, as shown in FIG. 2a. The slope of the capacitance change is proportional to the velocity of the sample in the measuring channel(3) and permits the calculation of the viscosity.

It is advantageous, and increases the accuracy of the device, if the height of the measuring channel(3) has the same value as the thickness of the cover layer(8') in FIG. 2.

The dielectric constant can be determined from the capacitance of the device as soon as the measuring channel(3) is completely filled with the sample.

FIG. 2b shows a possible design of the channel device where the substrate(1) consists of a basic material (ie. silicon or p-doped Si) (1') topped by an n-doped layer(1"), forming a barrier layer. Viscosity and dielectric constant measurements can be performed as described above.

Density measurements of the sample can be performed by the device shown in FIG. 3 and FIG. 3a. Transmitter(11) and receiver layers(12) are arranged on indentations or on the surface of a piezoelectric substrate. The transmitter layers(11) are connected to high frequency generators(13), supplying 20 to 50kHz in the low voltage range and generating surface accoustic waves in the substrate(1). The resonance signal, detected by the receiver layer(12), can be changed or damped in dependance of the density of the sample in the measuring channel(3).

Figure 4:
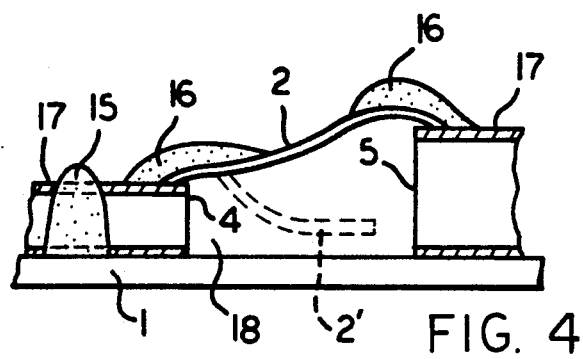
FIG. 4 is a view showing the connection of tubes to the substrate and channel layer by an adhesive layer.

FIG. 4 shows two tubes(17) connected to the substrate(1), ie. by an adhesive layer(15). The two tubes(17) are connected to a layer(2) which forms a channel(18) with the substrate(1), adhering tightly to the tubes(17) and the substrate(1) as well. The transition between the layer(2) and the tubes(17), kinks, exposed bends, etc. can be strengthened mechanically by supporting layers(16) consisting of the same material or a material different from that of layer(2). The fabrication of such a connection is performed by depositing a dissolvable substance onto the ends of the tubes(17) and onto the substrate(1) with the desired shape of the channel(18). The shape of the dissolvable substance can be obtained, for instance, by photolithographic processes. The layer(2) will be deposited onto the dissolvable substances in such a way that the layer(2) forms a tight connection with the tubes(17) and the substrate(1). The dissolvable substance will be dissolved through the tubes (17). This technique allows the design of connections between and to tubes of various, especially very small, dimensions.

Figure 5:
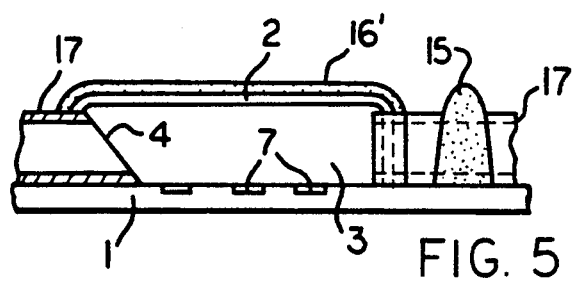
FIG. 5 is a cross-sectional view showing inlet and outlet tube positions relative to the sensor positions.

FIG. 5 shows a design, appropriate to forming inlet and outlet orifices(4,5) of measuring channels(3). The tubes(17) replace the orifices(4,5) in the substrate(1). The design of the measuring arrangement with sensors and actuators can be as described in FIGS. 1 to 3. The layers(2) can be covered by a protective layer(16') which can be deposited in the same way as layer(2) consisting of the same, or a different material (ie. glue), as layer(2). The endings of the tubes(17) can be tilted.

Figure 6:
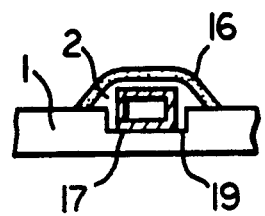
FIG. 6 is a side view depicting the indentation of the tubes in the substrate.
Figure 7:
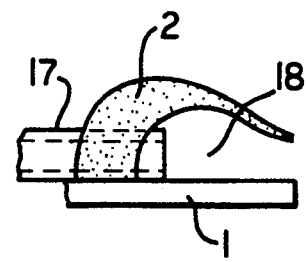
FIG. 7 schematically depicts the connection of the tube to the substrate via an adhesive layer.

FIG. 6 shows that the tubes (17), especially their endings, can be covered by the layer(2) and thereby tightly connected to the substrate(1). The layer(16) can be of additional support and increase the adhesion of the tubes(17) to the substrate(1). FIG. 6 also shows the tubes(17) can be placed in indentations(19) in the substrate(1). The cross section of the tubes(17) can be of any shape, ie. round, rectangular, etc. The same techinques which permit the production of tube connections also permit the fabrication of special tube continuations (FIG. 7): a tube(17) which can be connected by an adhesive layer to a substrate(1) will be covered at its one ending by a dissolvable substance which also covers the substrate(1), being especially shaped at this part, ie. like a nozzle. The layer(2) will be deposited onto at least part of the tube(17), at least parts of the dissolvable substance and at least parts of the substrate(1). The dissolvable substance will be dissolved, leaving a nozzle-like continuation of the tube(17), formed by the layers(2) and the substrate(1), and which can be used ie. for injection of substances into the body tissue, etc. A similar nozzle-like extension of the tube(17) is also shown in FIG. 4, created by the layer(2'), which can be mechanically protected and /or strengthened by an additional layer(16).

Figure 8:
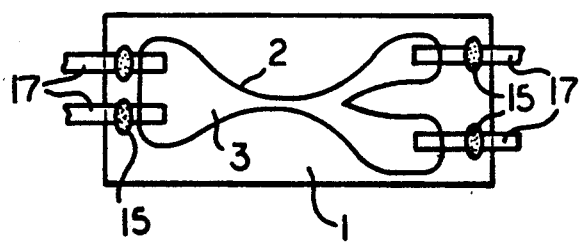
FIGS. 8 and 9 are top views of a multiple tube/multiple channel device. Preferred or advantageous arrangements of the invention, as well as the detailed procedures, are to be found in the sub-claims, the descriptions and the schematic drawings.

FIG. 8 shows several tubes(17) which are not necessarily arranged in parallel, and which are connected by a channel(3) which is formed by the layer(2) and the substrate(1). The endings of the tubes(17) on the left-hand side of FIG. 8 are combined by the measuring channel(3) of decreasing cross sections. The measuring channel(3) finally splits up into several channels which can have different cross sections, each of which can be connected to a tube(17). The described invention allows the fabrication of almost any kind of bifurcation, cross section and channel shape in order to establish connections of, and among, numerous tubes creating the possibility of forming valve-like control elements, flow regulators, etc.

It is also possible to etch the measuring channel (3) as shown in FIG. 8 into the substrate (1) in order to achieve a smooth transition between the tubes (17) and the measuring channel (3). Preferable diameters of the tubes (17) for the described fabrication procedures are in the range between 5 um and 500 um. It is also possible to connect two tubes (17) with each other which are placed next to each other or located in such a way that their ends are almost touching each other.

The invented channel devices and the tube connections can be used for investigations of body and tissue liquids, for delivery of substances to various ie. nerves, organs, etc. and for industrial applications, ie. ink jet recorders, fuel injection systems, or other devices where pipe systems, consisting of fine tubes, have to be connected to each other or external, macroscopic, supply systems. A big advantage of the invention is also that the described channel devices yield precise results also in case of extremely small sample volumes, representing unique measuring units regarding response time, accuracy, resolution and reproductibility.

The materials forming the layer (2) or (16) can consist of organic substances, such as synthetic resin, polymers, epoxy resin, ect. or any other organic substances such as $Si_3N_4$, $SiO_2$, $SiO$, $SiC$, ect. or substances with similar mechanical and or electrical qualities.

The connections to the sensors and actuators can be established by thin film interconnect paths, deposited in similar ways as described above.

It is, of course, possible that one measuring channel (3) contains several sensors and/or actuators and combinations thereof which can be arranged on and/or in the substrate (1) and/or on and/or in the layer (2).

Light sources and light detectors can be used for refraction index measurements: light can be, for instance, transferred through a light permeable layer (2) and light detectors will measure reflected and or transmitted light intensities which can be used, for instance, in order to calculate the refraction index of the sample. The light can also be transmitted through the tubes (17) or the tubes (17) can be replaced by optical fibers.

All these values, of course, can be used in order to determine and analyze the composition of the sample.

Figure 9:
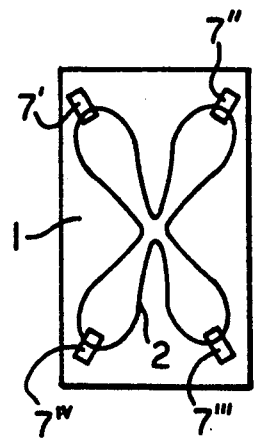

FIG. 9 shows a device for flow regulations; the flow of a sample, ie. from tube (17') to tube (17'') in the channel, formed by layer (2), can be changed or totally directed into the tube (17''''). Miniaturized valve and flow control units can be fabricated.

FIG. 3a shows, in dashed lines, the connections of the substrate (1) to a supporting substrate (1''') which ie. could be an IC socket, consisting of a gold plated surface, which can be, in a well known way, sealed to a Si substrate (1). Tubes can be soldered to the substrate (1''') forming inlet (4') and outlet (5') orifices for the measuring channel (3). the sensors can be connected via wires (21) through ceramic feed throughs (20).

A temperature sensor (22) and a heating layer (23) is shown in FIG. 2b allowing evaporation heat measurements. For that reason, a channel is filled with the sample, the temperature of which will be measured. The evaporating sample attracts evaporation heat from the environment, which can be measured by the sensor (22). The temperature slope is shown in FIG. 2a by the dashed line. The evaporation heat can be calculated from the time course of the temperature between To (temperature in the beginning of the measurement, where the measuring channel is filled with the sample) and T1 (end temperature, where the measuring channel is empty). Capacitance measurements can be performed at the same time, determining the amount of the substance in the channel, ect.

It is obvious that sensors and actuators, as shown in FIG. 2, can be arranged next and/or above each other.

BRIEF SUMMARY OF THE INVENTION

The invention discloses the construction of a channel device for the recording of thermal conductivity, viscoisty, density, dielectric constant, ect. of liquids and/or gases (sample), where the sample is directed through a measuring channel, with at least one inlet and one outlet orifice, containing at least one sensor unit and is characterized in that a measuring channel is established by the substrate and a layer, forming a wall, which is arranged in a certain, predetermined distance and fabricated ie. by evaporation, spin on, sputtering, drop on, ect. procedures, where the layers can consist of synthetic resin, glass, ceramic, ect. and in that measuring units are deposited in layers in and/or on the substrate and/or in and/or on the wall forming layer.

The invention also discloses the fabrication procedure for the channel device, characterized in that a dissolvable substance (ie. photoresist, syntethic resin, ect.) is deposited on a substrate, forming the inside of the measuring channel, on top of which a wall forming layer is deposited (by ie. spin on, drop on, evaporation, etc. techniques) where the layer not only covers at least part of the dissolvable substance but also at least a part of the substrate. The wall forming layer adheres well on the substrate and forms the measuring channel together with the substrate. The dissolvable substance can be dissolved and removed through the inlet and/or outlet orifices of the measuring channel.

The invention discloses furthermore a tube connection, characterized in that at least one tube, which can be connected with the substrate ie. by gravity forces, glue, ect. is covered by a layer, formed by drop on, evaporaton, sputtering, spin on, ect. procedures and which forms a tight seal with the tube and the substrate. The tube ending is kept open by the layer that, together with the substrate, forms a cavity which represents a continuation of the tube.

The invention also discloses the fabrication procedure of the tube connector, characterized in that on a substrate and at least one tube, which can be connected to the substrate, ie. by a glue, a dissolvable substance, ie. photoresist, synthetic resin, ect. is deposited forming a continuation of the tube. A layer is deposited on top of at least part of the dissolvable substance and on at least part of the tube and at least part of the substrate by ie. drop on, sputtering, spin on, etc. techniques which is tightly adhering on the tube and substrate; afterwards, the dissolvable substance is dissolved and removed through the tube or the orifice of the tube continuation, which is formed by the layer and the substrate.

I claim:

1. A method for manufacturing a device for measuring at least one characteristic of a fluid by passing such fluid through a measuring channel of appropriate dimensions for measuring such characteristic; said method comprising the steps of:
   providing a support member having an inlet orifice and an outlet orifice;
   depositing a channel-forming dissolvable material on the support member in a path which spans between the inlet and outlet orifices;
   controlling the shape of the path of dissolvable material to obtain a measuring channel having appropriate dimensions for measuring said one characteristic of the fluid;
   forming a wall by depositing a wall-forming material onto the support member and onto and around the path of passage-forming dissolvable material by a process selected from a group consisting of evaporation, spin on, drop on, sputtering, and reactive deposition, whereby a wall is formed which substantially covers the path of channel-forming dissolvable material and which covers at least parts of the support member;
   dissolving and removing the path of channel-forming dissolvable material through at least one of said orifices by introducing a solvent which dissolves the path of dissolvable material but which does not interact with the support member and the wall, whereby a measuring channel of appropriate dimensions is formed which spans between the inlet orifice and the outlet orifice, whereby inner surfaces of the support member and the wall define the measuring channel and whereby the support member and wall form a housing surrounding the measuring channel; and
   providing at least one sensor for measuring at least one characteristic of such fluid as it passes through the measuring channel by attaching and arranging the sensor in a sensing position relative to the housing by a process which is a member of a group consisting of evaporation, spin on, drop on, sputtering, reactive deposition, chemical vapor deposition, plasma enhanced chemical vapor deposition, and ion implantation whereby the housing and sensor form a sensor-housing unit.

2. The method as set forth in claim 1 wherein the step of forming the wall includes depositing on the dissolvable material a material selected from a group consisting of synthetic resin, glass, ceramic $Si_3N_4$, $SiO_2$, SiO, and combinations thereof.

3. The method as set forth in claim 1 further comprising the step of depositing a cover layer on top of at least a portion of said sensor-housing unit.

4. The method as set forth in claim 1 further comprising the step of etching the inner surfaces of the support surface and the wall which define the measuring channel.

5. The method as set forth in claim 1 further comprising the step of passivating the inner surfaces of the support surface and the wall defining the measuring channel.

6. The method as set forth in claim 1 wherein said step of providing a support member includes providing a substrate having two openings, one opening forming the inlet orifice and the other opening forming the outlet orifice.

7. The method as set forth in claim wherein said step of providing a support member includes the steps of:
   providing a substrate:
   attaching a first tube to the substrate to form the inlet orifice; and
   attaching a second tube to the substrate to form the outlet orifice.

8. The method as set forth in claim 1 wherein said step of dissolving and removing includes the step of removing said dissolvable material through at least one of said orifices.

9. The method as set forth in claim 1 wherein said step of providing a support surface includes the steps of:
   providing a substrate;
   attaching a plurality of tubes to the substrate to form a plurality of inlet orifices; and
   attaching a plurality of tubes to the substrate to form a plurality of outlet orifices.

10. The method as set forth in claim 1 wherein said step of providing a support member comprises the steps of providing a substrate; and attaching at least one tube to the substrate to form at least one of said orifices, and wherein the step of forming the wall includes the step of depositing the channel-forming dissolvable material on at least a portion of the tube.

11. The method as set forth in claim 10 wherein the step of attaching at least one tube to the substrate includes the step of attaching a tube having a nozzle-like opening.

12. The method as set orth in claim 10 further comprising the step of forming an indentation in the substrate for receiving the one tube.

13. A method of manufacturing a device for measuring at least one characteristic of a fluid by passing such fluid through a measuring channel of appropriate dimensions for measuring such characteristic, said method comprising the steps of:
  providing a substrate;
  attaching at least one tube to the substrate to form a first orifice;
  providing the substrate with a second orifice;
  depositing a channel-forming dissolvable material on the substrate in a path which is of a shape corresponding to such appropriate dimensions of such measuring channel of the measuring device and which spans between the first and second orifices;
  depositing a wall-forming material onto the path of the passage-forming dissolvable material and onto a portion of the tube by a process selected from a group consisting of evaporation, spin on, drop on, sputtering, reactive deposition, whereby a wall is formed which substantially covers the path of channel-forming dissolvable material and which covers a portion of the tube;
  dissolving and removing the channel-forming dissolvable material through at least one of the orifices by introducing a solvent which is capable of dissolving the dissolvable material but which does not interact with the substrate and the wall whereby the measuring channel of appropriate dimensions is formed which spans between the first and second orifices, and whereby the substrate, the tube and the wall form a housing surrounding the measuring channel;
  providing at least one sensor for measuring such one characteristic of such fluid as it passes through the measuring channel by attaching and arranging the sensor in a sensing position relative to the housing by a process selected from a group consisting of evaporation, spin on, drop on, sputtering, reactive deposition, chemical vapor deposition, plasma enhanced chemical vapor deposition, and ion implantation.

14. The method as set forth in claim 13 wherein said step of dissolving and removing includes the step of removing said dissolvable material through at least one of said orifices.

15. A method for manufacturing a device for measuring at least one characteristic of a fluid, said device having a wall defining a measuring channel of a certain shape, an inlet orifice and an outlet orifice for conducting fluid into and out of the measuring channel, and at least one sensor for measuring at least one characteristic so the fluid which flows through the measuring channel, said method comprising the steps of:
  providing a support member having an inlet orifice and an outlet orifice;
  depositing a channel-forming dissolvable material on the support member in a path which spans between the inlet and outlet orifices and having a shape corresponding to the shape of the measuring channel of the measuring device;
  controlling the shape of the path of dissolvable material to obtain a measuring channel having appropriate dimensions for measuring said one characteristic of the fluid;
  forming a wall by depositing a wall-forming material onto the support member and onto and around the path of passage-forming dissolvable material by a process selected from a group consisting of evaporation, spin on, drop on, sputtering, and reactive deposition, whereby a wall is formed which substantially covers the path of channel-forming dissolvable material and which covers at least parts of the support member;
  wherein this step of forming the wall includes depositing on the first body of dissolvable material the second body of material selected from a group consisting of synthetic resin, glass, ceramic $Si_3N_4$, $SiO_2$, SiO, and combinations thereof;
  dissolving and removing the path of channel-forming dissolvable material through at least one of said orifices by introducing a solvent which dissolves the path of dissolvable material but which does not interact with the support member and the wall, whereby a measuring channel of appropriate dimensions is formed which spans between the inlet orifice and the outlet orifice, whereby inner surfaces of the support member and the wall define the measuring channel and whereby the wall and the support member form a housing surrounding the measuring channel; and
  arranging and attaching at least one sensor in a sensing position relative to the housing by a process which is a member of group consisting of evaporation, spin on, drop on, sputtering, reactive deposition, chemical vapor deposition, plasma enhanced chemical vapor deposition, and ion implantation whereby the housing and sensor together form a sensor-housing unit; and
  depositing a cover layer on top of at least a portion of said sensor-housing unit.

* * * * *